United States Patent [19]

Gibbs

[11] Patent Number: 4,818,524
[45] Date of Patent: Apr. 4, 1989

[54] DEODORIZING COMPOSITIONS

[75] Inventor: Anthony Gibbs, Norwich, United Kingdom

[73] Assignee: Walex Products Company, Jamestown, N.C.

[21] Appl. No.: 70,911

[22] Filed: Jul. 8, 1987

[30] Foreign Application Priority Data

Jul. 9, 1986 [GB] United Kingdom ............... 8616740
Dec. 5, 1986 [GB] United Kingdom ............... 8629179

[51] Int. Cl.$^4$ ..................... A61K 31/55; A61K 7/32
[52] U.S. Cl. ................... 424/76.1; 424/76.21; 424/76.3; 424/76.6; 424/76.8; 514/635; 514/642; 514/643
[58] Field of Search ............. 424/76.1, 76.21, 76.3, 424/76., 76.8; 514/635, 642, 643

[56] References Cited

U.S. PATENT DOCUMENTS

| | | | |
|---|---|---|---|
| 4,014,676 | 3/1977 | Carter et al. | 514/635 |
| 4,202,882 | 5/1980 | Schwartz | 424/76.6 |
| 4,420,484 | 12/1983 | Gorman et al. | 514/635 |
| 4,478,821 | 10/1984 | Carillo | 514/635 |

Primary Examiner—Maurice J. Welsh
Assistant Examiner—S. A. Acquah
Attorney, Agent, or Firm—Ostrolenk, Faber, Gerb & Soffen

[57] ABSTRACT

The invention provides an odor neutralizing composition comprising:

(a) a complexing agent selected from a polymer of the formula (1)

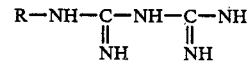

in which R is a substituted or unsubstituted alkylene group having up to 12 carbon atoms in the unsubstituted chain.

(b) a carrier capable of assisting wetting of odor forming compositions; and (c) a cationic moiety; said moiety being part of a chemically independent compound, or chemically associated with a complexing agent or the carrier.

12 Claims, No Drawings

DEODORIZING COMPOSITIONS

DESCRIPTION

This invention relates to deodorising compositions. Present technology in connection with odor control has generally been in the field of masking odors rather than actually neutralising them.

The present invention seeks in a first aspect to provide a broad spectrum deodorising composition.

According to a first aspect, therefore, of the present invention, there is provided an odor neutralizing composition characterised by:

(a) a complexing agent selected from a polymer of the formula (1):

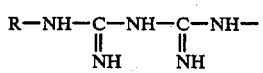

in which R is a substituted or unsubstituted alkylene group having up to 12 carbon atoms in the unsubstituted chain;

(b) a carrier capable of assisting wetting of odor forming compositions; and (c) a cationic moiety; said moiety being part of a chemically independent compound, or chemically associated with the complexing agent or the carrier.

The composition may additionally comprise a auxiliary complexing agent selected from a transition metal ion capable of oxidation, for example a divalent salt such as a reaction salt of iron, copper or gold. Suitable complexing agents for use in the inventive compositions as hereinbefore set forth may be the product of a reaction of transition metal salts with an organic acid such as citric, ascorbic or acetic acids.

In a second feature of the present invention, there is provided a deodorising composition comprising a complexing agent selected from one or more of an organic acid and a transition metal ion capable of oxidation; a carrier capable of assisting wetting of odor forming compositions, and a cationic moiety; said moiety being part of a chemically independent compound, or chemically associated with the carrier or complexing agent.

The compositions of the present invention include an effective amount of a wetting agent as a carrier, which may be cationic and serve as the cationic agent as well. Alternatively, the wetting agent may be a non-ionic or amphoteric detergent carrier, to assist in contact between the active ingredients of the composition of the invention and the article or surface to be deodorised. The compositions of the present invention may in certain circumstances be incorporated within an article such, for example, as a foam or sponge plastic of a textile material or the like to provide a more permanent deodorising action.

The precise mechanism whereby the composition in accordance with the present invention operates is not presently understood, but it is thought that the composition seeks to decompose or "attack" the odor forming constituent rather than simply mask the odor. It may do this by forming a complex with the odor forming compositions which reduces volatility, or odor forming abilities.

In a further embodiment of the invention, the composition may include an effective amount of an enzyme.

The composition in accordance with the present invention may be provided in a liquid or powder form.

When provided in a powder form the constituents of the composition are preferably adsorbed in a carrier powder. A typical powder in accordance with the present invention comprises sodium carbonate and sodium triphosphate; a cross-linked polyacrylamide, pumice dust, or keiselghur.

In a typical embodiment of the first aspect of the present invention, the composition comprises 20% to 80% by volume of the quaternary ammonium compound and 5% to 40% by volume of the polymer of formula (1) and up to 75% by volume of wetting agent. In the second aspect of the present invention, the composition generally comprises up to 10 parts by volume of the quaternary ammonium salt, although higher proportions of up to 50% are possible. The carrier may comprise up to 40 parts by volume while the complexing agent which is present at 100 parts by volume. The composition may be dilutable by up to 500% by volume of water. This produces a concentrate which may be subsequently diluted prior to use. The extent of dilution will depend on the circumstances and particular application of the composition in accordance with the present invention.

The quaternary ammonium compound is preferably a substituted or unsubstituted aromatic quaternary ammonium salt and is typically a substituted benzyl quaternary ammonium salt. In a specific embodiment of the invention, the quaternary ammonium salt is dimethyl benzyl ammonium chloride.

The polymer is preferably a polymeric biguanide having the general formula:

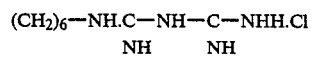

The wetting agent may be a cationic surfactant or a nonionic surfactant. Where the wetting agent is a nonionic surfactant it preferably has an H.L.B. within the range of 12 to 16 and preferably within the range of 13 to 15. A typical nonionic surfactant for use in accordance with the present invention is nonyl phenol ethylene oxide although it will be appreciated by the man skilled in the art that other surfactants of similar properties may be employed.

The compositions in accordance with the present invention have also been found to have disinfecting properties, and are particularly useful in the sterilization of medical equipment, especially when used in addition to other known disinfecting agents. The compositions have fungistatic and even fungicidal properties and therefore enjoy an odor control ability, and are also thought to be effective against, for example, athletes foot around swimming pools, changing rooms and sports areas.

In the powder form they can keep odor under control in sports footwear, while at the same time will reduce the possibility of infection from microorganisms which may develop in such footwear.

The compositions are effective in clinics, hospitals, homes for the aged and other people areas where odor control, for example, in the case of people having incontinency problems, is required.

The compositions may be sprayed onto furniture, upholstery fabrics, slippers, clothing, carpets all to prevent odor. In the latter application to carpets, control has been particular effective where pets or babies are known to cause odor problems.

Furthermore, the compositions may be employed in restaurants, hospitals, schools for the wiping of tables, furniture rails etc., to prevent and to remove odor and to inhibit the growth of microorganisms.

Where a cationic surfactant is employed, the composition can have antistatic properties as well as an odor control effects which makes it useful for inhibiting the build up of static electricity. The composition can be introduced into foams and sponges and are also used for the control of fish smells, toilet odors, control of damp and mold and bilge odors in boats.

Compositions formulated in accordance with the present invention have long shelf life and are stable at ordinary ambient temperatures. The composition tends to form in water soluble precipitates with anionic surfactants and soaps and also with strong alkalis and with complex phosphates.

The powder formulation in accordance with the present invention is readily soluble in hot, cold, fresh or salt water and a high degree of hardness has little, if any, depressant effect on any biocidal activity.

Following is a description by way of example only of methods of carrying the invention into effect.

EXAMPLE 1

A liquid formulation in accordance with the present invention was prepared as follows:

Dimethyl Benzyl Ammonium Chloride—35 liters
Polymeric Biguanide having the general chemical structure:

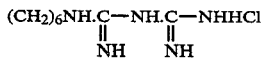

| Nonyl Phenol Ethylene Oxide | 15 liters |
| Water | 62.5 liters |
| | 137.5 liters |

The required volume of the quaternary ammonium compound, biguanide and surfactant are added to the tank and the required quantity of any marking dye is also added. The total volume is then made up to a total of 250 liters with filtered mains water. The liquid thus formed is stirred until uniform and the resultant liquid composition represents a super concentration of approximately 10 times normal use strength.

The composition is then diluted to normal strength and then packed with instruction for use.

EXAMPLE 2

A composition was prepared as follows:

| Dimethyl Benzyl Ammonium Chloride | 17.5 liters |
| Polymeric Biguanide having the general formula as set forth in Example 1 | 7.5 liters |
| Nonyl Phenol Ethylene Oxide | 31.25 liters |

The constituents were introduced into a tank of capacity of 250 liters, a small quantity of dye was added and water (193.75 liters) was then added to bring the volume up to 250 liters.

A powder composition was prepared as follows:

| Sodium Carbonate | 40 Kg. |
| Sodium Tripolyphosphate | 20 Kg. |
| Mixed composition as above | 20 liters. |

The solid ingredients were introduced into a mixer and the liquid composition is slowly introduced with mixing. On completion of the introduction of the liquid composition, the mixing was carried out for a further 60 minutes and then allowed to cool before passing through a vibrating sieve.

The composition has to be kept under dry conditions.

It has been found that the liquid composition of Example 1 and the powder composition of Example 2 are extremely effective in combatting odors. The powder composition produced in Example 2 is readily soluble in water, either hot or cold for direct application to on area in which an odor is to be treated.

EXAMPLE 3

Various odour-neutralising formulations are shown in Table A, hereinafter set forth. These formulations include a first component formed as follows:

Polymeric biguanide
Quaternery Ammonium Compound (Dimethyl Benzyl Ammonium Chloride)
Non-ionic surfactant
Water Depending upon the final product requirement the ratio of polymer to quaternary compound to surfactant can range, typically, as follows:

(1a) Low detergency low foam 5:20:0
(1b) Medium detergency low foam 5:40:2
(1c) High detergency medium foam 5:40:40

Various formulations are shown in Table A which follows:

TABLE A

| FORMULATION NO. | % BY VOL | ADDITIONAL COMPONENTS | % BY VOL. | WATER |
| --- | --- | --- | --- | --- |
| (1) 1(a) | 20% | Sodium Hydroxide | 2% | To 100% |
| low foam glass wash | | Non-ionic Surfactant | 2% | |
| (2) 1(a) | 10% | Non-ionic | 10% | " |
| wax deodorizer | | Non-ionic Fatty grey Carnuba wax | 60% | " |
| (3) 1(a) toilet fluid | 50% | Formaldehyde Non-ionic Surfactant | 10% 5% | " |
| (4) 1(a) toilet fluid (perfumed) | 40% | Isopropyl alcohol Perfume | 10% 2% | " |
| (5) 1(a) | 20% | Non-ionic | 20% | " |

TABLE A-continued

| FORMULATION NO. | % BY VOL | ADDITIONAL COMPONENTS | % BY VOL. | WATER |
|---|---|---|---|---|
| high temp (90° C.) high pressure Surgical wash | | Surfactant Sodium Hydroxide Antifoam | 2% as required | |
| (6) 1(a) ultrasound cleaning fluid | 10% | Non-ionic Surfactant Sodium Hydroxide | 20% 2% | " |
| (7) 1(a) Treatment of shipping containers as hot pressure washing fluid | 40% | Formaldehyde Non-ionic Surfactant | 2% 10% | |
| (8) 1(b) Descaler | 10% | Hydrochloric acid Non-ionic Surfactant | 9% 5% | NONE |
| (9) 1(b) Pipe & Pump cleaner | 10% | Non-ionic Surfactant Sodium Hydroxide | 10% 12% | To 100% |
| (10) 1(b) Optic cleaner | 5% | Non-ionic Surfactant Sodium Hydroxide | 10% 5% | " |
| (11) 1(C) Hard surface cleaner | 60% | Sodium Hydroxide | 2% | " |
| (12) 1(c) Hard glass wash fluid | 20% | Non-ionic Surfactant | 20% | " |
| (13) 1(c) Janitorial detergent | 40% | Non-ionic Surfactant | 20% | " |
| (14) 1(c) pre-soak cleaning fluid | 20% | Sodium Hydroxide Non-ionic Surfactant | 5% 10% | " |

ODOUR CONTROL BASE FORMULATION 2 - EXAMPLE 4
Components
Quarternery Ammonium Compound
Non-ionic surfactant
Citric acid
Sulphate The active components are citric acid and ferrous sulphate which are present as a 1:10 mole solution. The quaternary ammonium compound will enhance the odour neutralising effect as well as providing some biocidal and biostatic activity. The presence of non-ionic surfactants improves wetting and penetration as well as providing a degree of detergency. In general the quaternary ammonium compound can be incorporated up to 10% and non-ionic up to 40% (figures based on 100% active chemical).

TABLE B

| FORMULATION NO. 2 | % BY VOL. | ADDITIONAL COMPONENTS | % BY VOL. | WATER |
|---|---|---|---|---|
| (15) Glass wash without quaternary ammonium salt | 10% | Non-ionic Surfactant | 3% | to 100% |
| (16) Upholstery cleaner | 20% | Non-ionic Surfactant Isopropyl alcohol | 20% 5% | " |
| (17) Carpet Stain-remover | 50% | Citric acid (10 mole) | 15% | " |
| (18) Plastics cleaner | 20% | Non-ionic Surfactant Citric acid (10 mole) Antifoam | 10% 10% as required | " |

It will be noted that Example 15 provides an excellent glass wash without the quaternary ammonium salt utilizing solely the complex of the citric acid and metal complex, along with a suitable carrier.

The cleaners itemised in Table B are all satisfactory for the purposes set out in the left hand column.

What we claim is:

1. An odor neutralizing composition comprising
   (a) a complexing agent selected from a polymer of the formula (1)

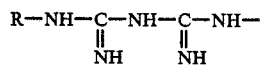

in which R is a substituted or unsubstituted alkylene group having up to 12 carbon atoms in the unsubstituted chain;
   (b) a carrier capable of assisting wetting of odor forming compositions;
   (c) a cationic moiety; said moiety being part of a chemically independent compound, or chemically associated with a complexing agent or the carrier, and
   (d) an auxiliary complexing agent selected from a transition metal ion which is capable of oxidation.

2. A composition according to claim 1 wherein the cationic moiety is associated with the complexing agent.

3. A composition according to claim 1 wherein the ion is derived from the reaction of an organic acid with a divalent transition metal salt.

4. A composition according to claim 1 comprising an auxiliary complexing agent selected from a quaternary ammonium salt and an organic acid.

5. A composition according to claim 4 wherein the quaternary ammonium salt is a substituted or unsubstituted aromatic quaternary ammonium salt, and the organic acid is selected from citric, ascorbic or acetic acids.

6. A deodorising composition comprising a complexing agent selected from one or more of an organic acid and a transition metal ion capable of oxidation; a carrier capable of assisting wetting of odor forming compositions, and a cationic moiety; said moiety being part of a chemically independent compound, or chemically associated with the carrier or complexing agent.

7. A composition according to claim 6 wherein the complexing agent is selected from a quaternary ammonium compound; and in that the transition metal ion is divalent and is derived from the product of a reaction between a source of transition metal ions and an organic acid.

8. A composition according to claim 7 wherein the quaternary ammonium compound is dimethylbenzyl ammonium chloride, the complexing agent is the reaction product of citric ascorbic or acetic acid and a reactive salt or ion copper or gold, and in that the carrier is a non-ionic or amphoteric surfactant.

9. An article impregnated with a composition according to claim 1.

10. A method of neutralizing odors which comprises exposing the odor to the odor neutralizing composition of claim 1.

11. A method of neutralizing odors which comprises exposing the odor to the odor neutralizing composition of claim 4.

12. A method of neutralizing odors which comprises exposing the odor to the odor neutralizing composition of claim 5.

* * * * *